United States Patent
Lue

(10) Patent No.: US 10,363,279 B2
(45) Date of Patent: Jul. 30, 2019

(54) TREATMENT AND PROPHYLAXIS FOR NEUROLOGICAL CONDITIONS AND DISEASES

(71) Applicant: NuBiome, Inc., Mountain View, CA (US)

(72) Inventor: Brian C. Lue, Mountain View, CA (US)

(73) Assignee: NuBiome, Inc., Mountain View, CA (US)

( * ) Notice: Subject to any disclaimer, the term of this patent is extended or adjusted under 35 U.S.C. 154(b) by 72 days.

(21) Appl. No.: 15/436,218

(22) Filed: Feb. 17, 2017

(65) Prior Publication Data

US 2017/0239302 A1    Aug. 24, 2017

Related U.S. Application Data

(60) Provisional application No. 62/297,831, filed on Feb. 20, 2016.

(51) Int. Cl.
*A61K 38/48*    (2006.01)
*A61K 35/747*   (2015.01)

(52) U.S. Cl.
CPC .......... *A61K 35/747* (2013.01); *A61K 38/482* (2013.01); *A61K 38/4886* (2013.01); *C12Y 304/21062* (2013.01); *C12Y 304/24* (2013.01)

(58) Field of Classification Search
None
See application file for complete search history.

(56) References Cited

U.S. PATENT DOCUMENTS

| 6,203,797 | B1 * | 3/2001 | Perry .................. A61K 31/198 424/639 |
| 6,696,057 | B1 * | 2/2004 | Bojrab ................. A61K 35/744 424/93.3 |
| 7,901,925 | B2   | 3/2011 | Bojrab |
| 8,927,242 | B2   | 1/2015 | Lue et al. |
| 2007/0298018 | A1 | 12/2007 | Bojrab |

OTHER PUBLICATIONS

Article entitled "Carbamazepine in the Treatment of Lyme Disease-Induced Hyperacusis" by J.A. Nields et. al. in The Journal of Neuropsychiatry & Clinical Neurosciences vol. 11, Iss. 1: 97-99, Feb. 1999.
Article entitled "Molecular mimicry revisited: gut bacteria and multiple sclerosis" by F.C. Westall in The Journal of Clinical Microbiology vol. 44, Iss. 6: 2099-2104, Jun. 2006.
Article entitled "Autoantibodies against neuropeptides are associated with psychological traits in eating disorders" by S.O. Fetissov et.al. in Proceedings of the National Academy of Sciences of the United States of America 102, Iss. 41: 14865-14870, Oct. 11, 2005.
Article entitled "Psychobiotics and the gut-brain axis: in the pursuit of happiness" by L. Zhou et. al. in Neuropsychiatric Disease and Treatment. 2015:11 715-723.
Article called "Probiotic Mixture KF Attentuates Age-Dependent Memory Deficit and Lipidemia in Fischer 344 Rats" by Jeong et. al. J. Microbiol. Biotechnol. (2015), 25(9), 1532-1536.
Article entitled "*Lactobacillus delbrueckii* ssp. *bulgaricus* B-30892 can inhibit cytotoxic effects and adhesion of pathogenic Clostridium difficile to Caco-2 cells" by P. Bannerjee et al. in Gut Pathogens 1:8, 2009.
Article entitled "Characterization of a novel Pep-F-like oligopeptidase secreted by Bacillus amyloliquefaciens" by Chao et al. in Applied Environ. Microbiol. 72: 968-971, 2006.
Article entitled "Overexpression of the PepF Oligopeptidase inhibits sporulation initiation in Bacillus subtilis" by Kanamaru et al. in J. Bacteriol. 184: 43-50, 2002.
Article entitled "Biochemical and Genetic Characterization of PepF, an Oligopeptidase from Lactococcus lactis" by Monnert et al. in J. Biol. Chem. 269: 32070-32076, 1994).
Article entitled "Cloning and expression of an oligopeptidase, PepO, with novel specificity from Lactobacillus rhamnosus HN001" by Christensson et al. in Applied Environ. Microbiol. 68: 254-262, 2002.
Article entitled "Enzymatic ability of *Bifidobacterium animalis* subsp. *lactis* to hydrolyze milk proteins: Identification and Characterization of Endopeptidase O" by Janer et al. in Applied Environ. Microbiol. 71: 8460-8465, 2005.
Article entitled "Genetic characterization and physiological role of endopeptidase O from Lactobacillus helveticus CNRZ32" by Chen et al. in Applied Environ. Microbiol. 64: 3411-3415, 1998.
Article entitled "Cloning and sequencing of the gene for a Lactococcal endopeptidase, an enzyme with sequence similarity to mammalian enkephalinase" by Mierau, et al. in J. Bacteriol. 175: 2087-2096, 1993).
Article entitled "Identification and characterization of Lactobacillus helveticu Pep O2 an endopeptidase with post proline specificity" by Chen et al. in Applied Environ. Microbiol. 69: 1276-1282, 2003.
Article entitled "Amyloid-degrading ability of nattokinase (subtilisin) from Bacillus subtilus natto" by Hsu et al. in J. Agricul. Food Chem. 57: 503-8, 2009).

* cited by examiner

Primary Examiner — Blaine Lankford
(74) Attorney, Agent, or Firm — Michael B. Einschlag

(57) ABSTRACT

An embodiment is a method of preventing, mitigating or treating neurological conditions and diseases that includes administering an effective amount of a medicament comprised of *Lactobacillus bulgaricus* B-30892 and/or a supernatant resulting from culturing *Lactobacillus bulgaricus* B-30892 and/or bioactive materials resulting from culturing *Lactobacillus bulgaricus* B-30892 to a human to prevent, mitigate or treat neurological conditions and diseases.

5 Claims, No Drawings

TREATMENT AND PROPHYLAXIS FOR NEUROLOGICAL CONDITIONS AND DISEASES

This patent application relates to U.S. Provisional Application No. 62/297,831 filed Feb. 20, 2016 from which priority is claimed under 35 USC § 119(e), and which provisional application is incorporated herein in its entirety.

BACKGROUND

Many neurological illnesses are caused by autoimmune reactions, toxins, and/or interfering chemistries to nervous tissue and neurological signaling chemistries and their receptors. Many of the sources of the harmful chemistries come from bacteria in the gastrointestinal tract. Some examples of such conditions are autism spectrum disorder, obsessive compulsive disorder, dyslexia, memory loss, ataxia, multiple sclerosis, anorexia nervosa, bulimia nervosa, tremor, depression, anxiety, mood swings, schizophrenia, Alzheimer' s Disease, and Celiac Disease (later referred to as "neurological conditions and diseases"). Autism Spectrum Disorder describes a constellation of symptoms such as persistent deficits in social communication and interaction, restricted or repetitive behavioral patterns, and significant impairments in social and occupational areas of functioning. Those deficits typically show up in the first three years of life. Dyslexia causes confusion in the ordering of letters while reading text. Researchers have reported treating dyslexia due to Lyme disease infection with the antibiotic cefotaxime (see an article entitled "Carbamazepine in the Treatment of Lyme Disease-Induced Hyperacusis" by J. A. Nields et. al. in The Journal of Neuropsychiatry & Clinical Neurosciences Vol 11, Iss. 1: 97-99, February 1999). Multiple Sclerosis has been shown to be associated with gut bacteria producing chemistries that cause cross-reactions to myelin (see an article entitled "Molecular mimicry revisited: gut bacteria and multiple sclerosis" by F. C. Westall. in The Journal of Clinical Microbiology Vol 44, Iss. 6: 2099-2104, June 2006). Anorexia nervosa and bulimia nervosa are caused by autoimmune reactions to the hormonal system responsible for appetite control and mood (see an article entitled "Autoantibodies against neuropeptides are associated with psychological traits in eating disorders" by S. O. Fetissov et. al. in Proceedings of the National Academy of Sciences of the United States of America 102, Iss. 41: 14865-14870, Oct. 11, 2005). Many reports have indicated that gut bacteria can cause depression, anxiety, and mood swings. Celiac Disease is caused by immune or hormonal reactions to certain subcomponents of the gluten molecule, some of which harm the nervous system.

Researchers have reported that microbial activities and compositions in the gut affect the nervous system. The researchers mentioned that a bacteria species called Alistipes from the phylum Bacteriodes is abnormally more plentiful in people with depression. Researchers have also reported abnormalities in the gut bacteria in mood disorders (for example, depression, anxiety and mood swings) may communicate with the brain via the vagus nerve. They also report that toxins produced by gut bacteria are believed to enter the bloodstream and cross through the blood-brain barrier (see an article entitled "Psychobiotics and the gut-brain axis: in the pursuit of happiness" by L. Zhou et. al. in Neuropsychiatric Disease and Treatment. 2015:11 715-723).

Present treatments for neurological conditions and diseases have primarily included the use of drugs. Some drugs used are chemicals that interact with the serotonin system in the brain. For example, in mood disorders such as depression and anxiety and/or eating disorders, Serotonin Reuptake Inhibitors SRIs can be prescribed. A problem with these approaches is that they come with serious side-effects and more importantly, since certain neurological conditions and diseases are caused by a neurotoxin and/or autoimmune reaction, the aforementioned drugs do not address the root cause of the problem, namely, a toxic response of or an immune reaction to the nervous system and its chemistries.

Studies have shown that certain probiotics, safe bacteria that confer benefit to a host, can improve neurological behavior in autism, anxiety, and memory. For example, a patent has been granted for its use in autoimmune obsessive compulsive disorder (see U.S. Pat. No. 8,927,242 entitled "Treatment and prophylaxis for obsessive compulsive disorder"). Researchers have found that probiotics can improve memory in rats (see an article called "Probiotic Mixture KF Attenuates Age-Dependent Memory Deficit and Lipidemia in Fischer 344 Rats" by Jeong et. al. J. Microbiol. Biotechnol. (2015), 25(9), 1532-1536)

SUMMARY

One or more embodiments of the present invention address root causes of one or more of the above-identified problems; namely, antigenic substances that cause the immune system to react with body tissues, i.e., (a) antigenic substances that cause the immune system to attack self tissues or chemistries in the brain or other parts of the nervous system; and/or (b) neurotoxins that affect the nervous system. In particular, it is believed that improperly behaving bacteria, or suboptimal populations of bacteria, are and/or create antigenic and/or toxic substances that cause neurological conditions and diseases. In accordance with one or more embodiments, administering an effective amount of a medicament to a human comprised of *Lactobacillus bulgaricus* (formerly called *Lactobacillus delbrueckii* sub sp. *bulgaricus*) B-30892 and/or a supernatant resulting from culturing *Lactobacillus bulgaricus* B-30892 and/or bioactive materials resulting from culturing *Lactobacillus bulgaricus* B-30892 to prevent, mitigate or treat neurological conditions and diseases.

According to an in vitro study of *L. bulgaricus* B-30892, *L. bulgaricus* B-30892 secretes chemistries capable of neutralizing the *Clostridia difficile* toxins A and B (see an article entitled "*Lactobacillus delbrueckii* ssp. *bulgaricus* B-30892 can inhibit cytotoxic effects and adhesion of pathogenic *Clostridium difficile* to Caco-2 cells" by P. Bannerjee et al. in Gut Pathogens 1:8, 2009). Thus, it is believed that *L. bulgaricus* B-30892 may secrete chemistries that neutralize toxins that cause or exacerbate neurological conditions and diseases. In order to interfere with neurotoxins and/or reduce antibody production, in accordance with one or more of such embodiments, bacteria and/or enzymes that interfere with neurotoxins and proline containing autoimmune mimics are used. In accordance with one or more embodiments, an effective amount of a medicament comprised of one or more suitable bacteria and/or one or more suitable enzymes is administered to a person (or other mammal) to prevent, mitigate or treat neurological conditions and diseases. An example of one suitable bacterium is, but is not limited to, *Lactobacillus bulgaricus* B-30892. A drinkable yogurt containing *Lactobacillus bulgaricus* B-30892, called Liovi™ Probiotic Drink, is commercially available from NuBiome, Inc. (Palo Alto, Calif.).

DETAILED DESCRIPTION

In the gastrointestinal tract ("GI" or "gut"), bacteria produce chemicals, and bacteria die and break up into smaller pieces. In certain instances, the immune system generates antibodies against the bacteria, one or more of the chemicals and/or the smaller pieces (all such bacteria, smaller pieces and chemicals being referred to as "antigenic substances") where the antibodies confuse the antigenic substances with self-molecules. As such, when the immune system attacks the antigenic substances it also attacks self-molecules, and results in an autoimmune disease. In other cases gut bacteria can affect the amount of neurotransmitters such as dopamine and seratonin produced and/or residing in and around the gastrointestinal tract.

Some probiotic bacteria may produce enzymes and other chemicals in the gut that are capable of breaking down or neutralizing the antigenic substances. Some probiotic bacteria may reduce the number or activity of bacteria and/or other microorganisms that are themselves antigenic substances or provide antigenic substances by competing in the gut for energy sources or space for antigenic bacteria. And some probiotic bacteria may communicate with a host immune system to create molecules capable of interfering with harmful antigenic substances. And some probiotic bacteria can help to normalize the amount of neurotransmitters.

One or more embodiments address root causes of one or more of the above-identified problems; namely, antigenic substances that cause the immune system to react with body tissues, i.e., (a) antigenic substances that cause the immune system to attack self tissues or chemistries in the brain or other parts of the nervous system; and/or (b) neurotoxins that affect the nervous system. Further, in accordance with one or more such embodiments, one can neutralize problematic antigenic substances, i.e., one can prevent/mitigate/treat an autoimmune disease without suppressing the immune system and, thereby, prevent an increased risk of infection or cancer arising from suppression of the immune system.

One or more embodiments of the present invention address an autoimmune response and/or toxins against nervous system tissues, chemistries, and receptors. To reduce/neutralize activity of such antigenic and/or toxic substances (for example, to reduce antibody production, and hence, an autoimmune response thereto), in accordance with one or more embodiments, an effective amount of a medicament comprised of a probiotic bacterium, a supernatant of the probiotic bacterium, bioactive materials from an extract of the supernatant, and/or an enzyme is administered to the gut. In accordance with one or more such embodiments, it is believed that when proper ones of the above are administered, the antigenic substances are neutralized or destroyed (for example, by interfering with and/or reducing their population before they encounter the immune system) and, thereby, prevented or inhibited from triggering the immune system. In the case of neurological conditions and diseases, it is believed that the antigenic substances cause the creation of cross-reacting antibodies to brain structures such as the amygdala. In accordance with one or more such embodiments, it is believed that some antigenic substances are broken up into smaller chemical pieces that the immune system does not confuse with self-molecules. Further, in accordance with one or more such embodiments, it is believed that some antigenic substances are broken up into smaller chemical pieces that the immune system does not confuse with self-molecules. Still further, in accordance with one or more such embodiments, it is believed that some antigenic substances are attached to other chemicals that change antigenic chemical shapes sufficiently so that the immune system will not be triggered thereby. Still further, in accordance with one or more such embodiments, bacteria that secrete anti-toxins, compete for space and resources, and prevent the adhesion of harmful bacteria to human tissue in the gastrointestinal tract are used.

During a fermentation process for culturing probiotic bacteria, as the probiotic bacteria grow and multiply, the probiotic bacteria secrete bioactive materials into a liquid surrounding the probiotic bacteria. To obtain a supernatant, the probiotic bacteria are removed from the liquid by processes such as, for example and without limitation, centrifuging, filtering, or other separation process—the remaining liquid is the supernatant. The resulting supernatant contains bioactive materials such as, for example and without limitation, enzymes, proteins, peptides, hormones, vitamins, toxins, and other chemicals. The bioactive materials can be further purified by membrane purification techniques such as, for example and without limitation, reverse osmosis, distillation, chromatography, or other purification techniques. The liquid supernatant or extracted liquids can also be dried into a powder by freeze, ribbon/belt, or spray drying.

One or more embodiments of the present invention address root causes of one or more of the above-identified problems, namely, an autoimmune response against structures and chemistries used by the nervous system. To reduce antibody production, and hence, the autoimmune response thereto, in accordance with one or more such embodiments, bacteria that interfere with and/or reduce the population of bacteria before they encounter the immune system are used. It is believed that bacteria can create cross-reacting antibodies to brain structures such as the amygdala and/or basal ganglia.

In accordance with one or more embodiments, an effective amount of a medicament comprised of one or more suitable bacteria is administered to a person (or other mammal) to prevent, mitigate or treat neurological conditions and diseases. Such neurological conditions and diseases include: autism spectrum disorder, obsessive compulsive disorder, dyslexia, memory loss, ataxia, multiple sclerosis, anorexia nervosa, bulimia nervosa, tremor, mood disorders (where depression, anxiety and mood swings are considered mood disorders), schizophrenia, Alzheimer's Disease, and Celiac Disease. An example of one such bacterium is, but is not limited to, *Lactobacillus bulgaricus* (formerly called *Lactobacillus delbrueckii* subsp. *bulgaricus*) B-30892 ("*L. bulgaricus* B-30892"). *Lactobacillus bulgaricus* B-30892 is a non-pathogenic lactic acid producing bacteria that is used to culture commercial dairy products (for example, yogurt) food products for human and mammalian consumption. Its traits include, for example, secretion of anti-toxins to the *Clostridium difficile* (*C. diff*) toxins A and B, and an ability to interfere with adhesion of *C. diff* to caco-2 cells in vitro. *Lactobacillus bulgaricus* B-30892 is commercially available from NuBiome, Inc. of Palo Alto, Calif., USA. An effective amount of *L. bulgaricus* B-30892 contained in the medicament is in a range from about $1\times10^5$ to about $1\times10^{12}$ colony forming units (CFU) of *L. bulgaricus* B-30892 per day.

One case report relates to a six (6) year old male with autistic spectrum disorder and lack of verbal activity. Prior to consuming *L. bulgaricus* B-30892 he rarely uttered oral sounds. Within 11 days of consuming one (1) cup a day of a drinkable yogurt containing *L. bulgaricus* B-30892 (Liovi™ Probiotic Drink)—one cup contained approximately $19\times10^9$ CFU of *L. bulgaricus* B-30892, his mother reported a dramatic increase in his verbal activity. She reported that he began to babble, sing, and talk all day long.

Another case report relates to a six (6) year old male with autistic spectrum disorder with difficulty socializing with his peers and sister without being very disruptive. His father related that he consumed a half of a cup each day of a drinkable yogurt containing *L. bulgaricus* B-30892 (Liovi™ Probiotic Drink)—one cup contained approximately $19 \times 10^9$ CFU of *L. bulgaricus* B-30892, and after the fourth day, the son started to play with his sister peaceably. After two and a half months, other parents at the young boy's school were asking what happened to the boy because he was behaving better. After eight months his father said his teacher had no complaints regarding his son's behavior. Another case report relates to a forty-six (46) year old male who had age-related memory loss. After consuming 1 cup a day of a drinkable yogurt containing *L. bulgaricus* B-30892 (Liovi™ Probiotic Drink)—one cup contained approximately $19 \times 10^9$ CFU of *L. bulgaricus* B-30892—for six months, he related that he could remember telephone numbers, passwords, street addresses, and names much more often than before consuming the drinkable yogurt.

In accordance with one or more such embodiments, an effective amount of a medicament comprised of *Lactobacillus bulgaricus* bacteria (*L. bulgaricus* B-30892) is administered to a person (or other mammal) suffering from neurological conditions and diseases. An effective amount of *L. bulgaricus* B-30892 contained in the medicament is in a range from about $1 \times 10^5$ to about $1 \times 10^{12}$ colony forming units (CFU) of *L. bulgaricus* B-30892 per day in a cultured liquid and is in a range from about $1 \times 10^5$ to about $1 \times 10^{14}$ colony forming units (CFU) of *L. bulgaricus* B-30892 per day in a powdered form.

Because antigenic substances (also referred to as immunogens, mimics and/or antigens) for a disease can stimulate the production of antibodies to the nervous system, further embodiments include medicaments which: (a) contain one or more enzymes capable of breaking down antigenic substances—especially hard to digest proline containing peptides; and/or (b) contain one or more live and/or dead bacteria or portions of such bacteria capable of producing one or more enzymes capable of breaking down immunogens, mimics and/or antigens—especially hard to digest proline containing peptide antigenic substances. In particular, one or more embodiments comprise: (a) the use of one or more such enzymes by themselves or in concert with *L. bulgaricus* B-30892; and/or (b) the use of one or more bacteria capable of producing one or more such enzymes that break down these antigenic substances mimics, immunogens and/or antigens by themselves or in concert with *L. bulgaricus* B-30892. Examples of suitable such enzymes include, but are not limited to, oligopeptidase F (PepF) (see an article entitled "Characterization of a novel Pep-F-like oligopeptidase secreted by *Bacillus amyloliquefaciens*" by Chao et al. in *Applied Environ. Microbiol.* 72: 968-971, 2006; an article entitled "Overexpression of the PepF Oligopeptidase inhibits sporulation initiation in *Bacillus subtilis*" by Kanamaru et al. in *J. Bacteriol.* 184: 43-50", 2002; and an article entitled "Biochemical and Genetic Characterization of PepF, an Oligopeptidase from *Lactococcus lactis*" by Monnert et al. in J. Biol. Chem. 269: 32070-32076, 1994); endopeptidase O (PepO) (see an article entitled "Cloning and expression of an oligopeptidase, PepO, with novel specificity from *Lactobacillus rhamnosus* HN001" by Christensson et al. in *Applied Environ. Microbiol.* 68: 254-262, 2002;an article entitled "Enzymatic ability of *Bifidobacterium animalis* subsp. *Lactis* to hydrolyze milk proteins: Identification and Characterization of Endopeptidase O" by Janer et al. in *Applied Environ. Microbiol.* 71: 8460-8465, 2005; an article entitled "Genetic characterization and physiological role of endopeptidase O from *Lactobacillus helveticus* CNRZ32" by Chen et al. in *Applied Environ. Microbiol.* 64: 3411-3415, 1998; and an article entitled "Cloning and sequencing of the gene for a *Lactococcal* endopeptidase, an enzyme with sequence similarity to mammalian enkephalinase" by Mierau, et al. in *J. Bacteriol.* 175: 2087-2096, 1993); endopeptidase O2 (PepO2) (see an article entitled "Identification and characterization of *Lactobacillus helveticu* Pep O2 an endopeptidase with post proline specificity" by Chen et al. in *Applied Environ. Microbiol.* 69: 1276-1282, 2003) and subtilisin (see an article entitled "Amyloid-degrading ability of nattokinase (subtilisin) from *Bacillus subtilus* natto" by Hsu et al. in *J. Agricul. Food Chem.* 57: 503-8, 2009). One of ordinary skill in the art can readily purchase these enzymes commercially or fabricate them using methods that are well known to those of ordinary skill in the art. In accordance with one or more such embodiments, an effective amount of a medicament comprised of one or more enzymes capable of breaking down antigenic substances is administered to a human (or other mammal) suffering from neurological conditions and diseases. Examples of such enzymes include, but not limited to, PepF, PepO, PepO2 and subtilisin. In addition, in accordance with one or more further embodiments, an effective amount of a medicament comprised of *Lactobacillus bulgaricus* (*L. bulgaricus* B-30892) and/or its supernatant and/or one or more bacteria capable of producing one or more enzymes capable of breaking down antigenic substances is administered to a human (or other mammal) suffering from neurological conditions and diseases. An effective amount of *L. bulgaricus* B-30892 contained in the medicament is in a range from about $1 \times 10^5$ to about $1 \times 10^{12}$ colony forming units (CFU) and/or bacteria producing one or more enzymes capable of breaking down immunogens, mimics and/or supernatant resulting from culturing about $1 \times 10^5$ to about $1 \times 10^{12}$ colony forming units (CFU) of *L. bulgaricus* B-30892 per day is administered to a human (or other mammal) suffering from neurological conditions and diseases. Examples of such enzymes include, but not limited to, PepF, PepO, PepO2 and subtilisin.

In accordance with one or more further such embodiments, a medicament comprised: (a) of an effective amount of a supernatant of one or more suitable bacteria and/or one or more enzymes is administered to a human (or other mammal) to prevent/treat/cure neurological conditions and diseases; and/or (b) of an effective amount of one or more bacteria capable of producing an effective amount of one or more enzymes is administered to a human (or other mammal) to prevent/treat/cure neurological conditions and diseases. Further, in accordance with one or more further such embodiments: (a) an effective amount of the supernatant and/or one or more enzymes is an amount of the one or more enzymes (for example, in sufficient volume and/or concentration) that is effective in destroying or deactivating immunogens, mimics or antigens that cause or exacerbate neurological conditions and diseases; and/or (b) an effective amount of the one or more bacteria capable of producing one or more enzymes is an amount of the one or more bacteria (for example, in sufficient concentration) that is effective in producing an amount of the one or more enzymes effective in destroying or deactivating immunogens, mimics or antigens that cause or exacerbate neurological conditions and diseases.

In accordance with one or more further embodiments, a medicament comprised of an effective amount of oligopeptidase F (PepF) is administered to a patient to prevent/treat/ cure neurological conditions and diseases. In accordance with one or more such embodiments, an effective amount of oligopeptidase F (PepF) will depend upon the severity of the disease process (the PepF may be administered in one or more, preferably three, doses daily). However, an effective amount of PepF (for example, in sufficient concentration) is in a range from about 20 units/day to about 200 units/day, where the definition of a unit is an amount of PepF required to cleave one micromole of bradykinin at a pH of 8.0 and a temperature of 40° C.

In accordance with one or more embodiments, an effective amount of PepF in combination with the *L. bulgaricus* B-30892 strain and/or a supernatant of the *L. bulgaricus* B-30892strain will be administered, and the amount will depend upon the severity of the disease process (the PepF and *L. bulgaricus* B-30892 and/or the supernatant may be administered one or more, preferably three, doses daily). An effective amount of *L. bulgaricus* B-30892 contained in the medicament is in a range from about $1\times10^5$ to about $1\times10^{12}$ colony forming units (CFU) of *L. bulgaricus* B-30892 per day and/or supernatant resulting from culturing about $1\times10^5$ to about $1\times10^{12}$ colony forming units (CFU) of *L. bulgaricus* B-30892 per day in a cultured liquid and is in a range from about $1\times10^5$ to about $1\times10^{14}$ colony forming units (CFU) of *L. bulgaricus* B-30892 per day in a powdered form.

PepF belongs to the M3 metalloprotease family. While most bacterial PepFs are cytoplasmic endopeptidases, some are secreted; for example, the enzyme from *Bacillus amyloliquefaciens*. PepF has been seen in a variety of bacterial genuses including, *Lactococcus* and *Bacillus* and in *Bacillus subtilis*. In accordance with one or more embodiments, a medicament comprised of an effective amount of a non-pathogenic microorganism and/or its spores (that are capable of providing PepF) is administered to a patient to prevent/treat/cure neurological conditions and diseases. In accordance with one or more such embodiments, the microorganism and spores include, for example and without limitation, one or more of *Lactobacillus jensenii, Lactobacillus crispatus, Lactobacillus johnsonii, Lactobacillus plantarum, Lactobacillus helveticus, Lactobacillus amylolyticus, Lactobacillus salivarius, Lactobacillus ultunensis, Lactobacillus rhamnosus, Lactobacillus acidophilus, Lactobacillus delbrueki bulgaricus, Lactobacillus gasseri, Lactobacillus casei, Lactobacillus coleohominis, Lactobacillus fermentum, Lactobacillus paracasei, Lactococcus lactis cremoris, Enterococcus faecalis, Bacillus cereus* (spore-forming), *Campylobacter subtilisis*, and *Oenococcus oeni* and their various strains. An effective amount of the microorganism and/or its spores is an amount that is effective to cause destruction or deactivation of mimics, immunogens and/or antigens that cause or exacerbate neurological conditions and diseases. In accordance with one or more such embodiments, an effective amount is from about 100 thousand CFU to about 600 billion CFU per dose, where the dose is administered about one or more times per week, or as often as about one to three times daily.

In accordance with one or more embodiments, a medicament comprised of an effective amount of parts of, or entirely broken up, microorganisms and/or their spores (that are capable of providing PepF) is administered to a patient to prevent/treat/cure neurological conditions and diseases. Parts of the microorganisms and/or spores can be separated and selected, using any one of a number of methods that are well known to those of ordinary skill in the art, for their bioactive properties to help ensure and improve the rate of the destruction or deactivation of mimics, immunogens and/or antigens that cause or exacerbate neurological conditions and diseases and/or to improve the effectiveness of enzymes in the gastrointestinal or respiratory tract in destroying or deactivating such mimics, immunogens and/or antigens. In accordance with one or more such embodiments, the microorganism and spores include, for example and without limitation, one or more of *Lactobacillus jensenii, Lactobacillus crispatus, Lactobacillus johnsonii, Lactobacillus plantarum, Lactobacillus helveticus, Lactobacillus amylolyticus, Lactobacillus salivarius, Lactobacillus ultunensis, Lactobacillus rhamnosus, Lactobacillus acidophilus, Lactobacillus delbrueki bulgaricus, Lactobacillus gasseri, Lactobacillus casei, Lactobacillus coleohominis, Lactobacillus fermentum, Lactobacillus paracasei, Lactococcus lactis cremoris, Enterococcus faecalis, Bacillus cereus* (spore-forming), and *Oenococcus oeni* and their various strains. An effective amount of the parts of, or entirely broken up, microorganisms and/or their spores is an amount sufficient to cause destruction or deactivation of mimics, immunogens and/or antigens that cause or exacerbate neurological conditions and diseases. In accordance with one or more such embodiments, an effective amount of parts or entirely broken up microorganisms is from about 100 thousand CFU to about 600 billion CFU per dose, where the dose is administered about one or more times per week, or as often as about one to three times daily. Methods for breaking up suitable microorganisms and/or spores include, for example and without limitation, sonication, crushing, shearing, oxidation, exposure to photonic radiation or chemical (for example, not limited to, enzymic) cleavage of the microorganisms.

In accordance with one or more embodiments, an effective amount of endopeptidase O (PepO) administered will depend upon the severity of the disease process (the PepO may be administered in one or more, and preferably three, doses daily). However, an effective amount of PepO is in a range from about 20 units/day to about 200 units/day, where the definition of a unit is an amount of PepO required to cleave one micromole of bradykinin at a pH of 6.0 and a temperature of 25° C.

In accordance with one or more embodiments, an effective amount of endopeptidase O (PepO in combination with the *L. bulgaricus* B-30892 strain and/or a supernatant of the *L. bulgaricus* B-30892 strain), will be administered, and the amount will depend upon the severity of the disease process (the PepO and *L. bulgaricus* B-30892 and/or the supernatant may be administered in one or more, and preferably three, doses daily). An effective amount of *L. bulgaricus* B-30892 contained in the medicament is in a range from about $1\times10^5$ to about $1\times10^{12}$ colony forming units (CFU) of *L. bulgaricus* B-30892 per day and/or supernatant resulting from culturing about $1\times10^5$ to about $1\times10^{12}$ colony forming units (CFU) of *L. bulgaricus* B-30892 per day in a cultured liquid and is in a range from about $1\times10^5$ to about $1\times10^{14}$ colony forming units (CFU) of *L. bulgaricus* B-30892 per day in a powdered form. An effective amount of PepO is in a range from about 20 units/day to about 200 units/day, where the definition of a unit is an amount of PepO required to cleave one micromole of bradykinin at a pH of 6.0 and a temperature of 25° C.

In accordance with one or more embodiments, a medicament comprised of an effective amount of a non-pathogenic microorganism and/or its spores (that are capable of providing PepO) is administered to a patient to prevent/treat/cure neurological conditions and diseases. PepO is found in a large range of bacterial systems. In accordance with one or more such embodiments, the microorganism and spores include, for example and without limitation, *Lactobacillus sanfrancisens, Lactobacillus plantarum, Lactobacillus acidophilus, Lactobacillus helveticus, Lactobacillus casei, Lactobacillus reuteri, Lactobacillus salivarius, Lactobacillus gasseri, Lactobacillus rhamnosus, Lactobacillus johnsonii, Lactobacillus jensenii, Lactobacillus amylolyticus, Lactobacillus sakei, Lactobacillus antrii, Lactobacillus paracasei, Lactobacillus ruminis, Lactococcus lactis, Bifidobacterium dentium, Bifidobacterium longum, Bifidobacterium adolescentis, Bifidobacterium animalis,* and *Oenicoccus oeni* and their various strains. An effective amount of the microorganism and/or its spores is an amount that is effective to cause destruction or deactivation of mimics, immunogens and/or antigens that cause or exacerbate neurological conditions and diseases. In accordance with one or more such embodiments, an effective amount is from about 100 thousand CFU to about 600 billion CFU per dose, where the dose is administered about one or more times per week, or as often as about one to three times daily.

In accordance with one or more embodiments, a medicament comprised of an effective amount of parts of, or entirely broken up, microorganisms and/or their spores (that are capable of providing PepO) is administered to a patient to prevent/treat/cure neurological conditions and diseases. Parts of the microorganisms and/or spores can be separated and selected, using any one of a number of methods that are well known to those of ordinary skill in the art, for their bioactive properties to help ensure and improve the rate of the destruction or deactivation of mimics, immunogens or immunogens that cause or exacerbate neurological conditions and diseases and/or to improve the effectiveness of enzymes in the gastrointestinal or respiratory tract in destroying or deactivating such mimics, immunogens and/or antigens. In accordance with one or more such embodiments, the microorganism and spores include, for example and without limitation, *Lactobacillus sanfrancisens, Lactobacillus plantarum, Lactobacillus acidophilus, Lactobacillus helveticus, Lactobacillus casei, Lactobacillus reuteri, Lactobacillus salivarius, Lactobacillus gasseri, Lactobacillus rhamnosus, Lactobacillus johnsonii, Lactobacillus jensenii, Lactobacillus amylolyticus, Lactobacillus sakei, Lactobacillus antri, Lactobacillus paracasei, Lactobacillus ruminis, Lactococcus lactis, Bifidobacterium dentium, Bifidobacterium longum, Bifidobacterium adolescentis, Bifidobacterium animalis,* and *Oenicoccus oeni* and their various strains. An effective amount of the parts of, or entirely broken up, microorganisms and/or their spores is an amount sufficient to cause destruction or deactivation of mimics, immunogens and/or antigens that cause or exacerbate neurological conditions and diseases. In accordance with one or more such embodiments, an effective amount of parts or entirely broken up microorganisms is from about 100 thousand CFU to about 600 billion CFU per dose, where the dose is administered about one or more times per week, or as often as about one to three times daily. Methods for breaking up suitable microorganisms and/or spores include, for example and without limitation, sonication, crushing, shearing, oxidation, exposure to photonic radiation or chemical (for example, not limited to, enzymic) cleavage of the microorganisms.

In accordance with one or more further embodiments, a medicament comprised of an effective dose of endopeptidase O2 (PepO2) from *Bifidobacterium animalis* subsp *lactis* is administered to a patient to prevent/treat/cure neurological conditions and diseases. Such PepO2 will destroy potential mimics, immunogens and/or antigens prior to immune activation.

In accordance with one or more embodiments, an effective amount of endopeptidase O2 (PepO2) administered will depend upon the severity of the disease process (the PepO2 may be administered in one or more, and preferably three, doses daily). However, an effective amount is in a range from about 20 units/day to about 200 units/day, where the definition of a unit is an amount of PepO2 required to cleave one micromole of BCN (f193-209) at a pH of 6.5 and a temperature of 25° C.

In accordance with one or more embodiments, an effective amount of PepO2 in combination with the *L. bulgaricus* B-30892 strain and/or a supernatant of the *L. bulgaricus* B-30892strain will be administered, and the amount will depend upon the severity of the disease process (the PepO2 and *L. bulgaricus* B-30892 and/or the supernatant may be administered one or more, preferably three, doses daily). An effective amount of *L. bulgaricus* B-30892 contained in the medicament is in a range from about $1\times10^5$ to about $1\times10^{12}$ colony forming units (CFU) of *L. bulgaricus* B-30892 per day and/or supernatant resulting from culturing about $1\times10^5$ to about $1\times10^{12}$ colony forming units (CFU) of *L. bulgaricus* B-30892 per day in a cultured liquid and is in a range from about $1\times10^5$ to about $1\times10^{14}$ colony forming units (CFU) of *L. bulgaricus* B-30892 per day in a powdered form.

In accordance with one or more embodiments, a medicament comprised of an effective amount of a non-pathenogenic microorganism and/or its spores (that are capable of providing PepO2) is administered to a patient to prevent/treat/cure neurological conditions and diseases. In accordance with one or more such embodiments, the microorganism and spores include, for example and without limitation, *Lactococcus lactis cremoris, Lactobacillus helveticus,* and *Lactobacillus johnsonii* and their various strains. An effective amount of the microorganism and/or its spores is an amount that is effective to cause destruction or deactivation of mimics, immunogens and/or antigens that cause or exacerbate neurological conditions and diseases. In accordance with one or more such embodiments, an effective amount is from about 100 thousand CFU to about 600 billion CFU per dose, where the dose is administered about one or more times per week, or as often as about one to three times daily.

In accordance with one or more embodiments, a medicament comprised of an effective amount of parts of, or entirely broken up, microorganisms and/or their spores (that are capable of providing PepO2) is administered to a patient to prevent/treat/cure neurological conditions and diseases. Parts of the microorganisms and/or spores can be separated and selected, using any one of a number of methods that are well known to those of ordinary skill in the art, for their bioactive properties to help ensure and improve the rate of the destruction or deactivation of mimics, immunogens or immunogens that cause or exacerbate neurological conditions and diseases and/or to improve the effectiveness of enzymes in the gastrointestinal or respiratory tract in destroying or deactivating such mimics, immunogens and/or antigens. In accordance with one or more such embodiments, the microorganism and spores include, for example and without limitation, *Lactococcus lactis cremoris, Lactobacillus helveticus,* and *Lactobacillus johnsonii* and their various strains. An effective amount of the parts of, or entire broken up, microorganisms and/or their spores is an amount sufficient to cause destruction or deactivation of mimics, immunogens and/or antigens that cause or exacerbate neurological conditions and diseases. In accordance with one or more such embodiments, an effective amount of parts or entirely broken up microorganisms is from about 100 thousand CFU to about 600 billion CFU per dose, where the dose is administered about one or more times per week, or as often as about one to three times daily. Methods for breaking up suitable microorganisms and/or spores include, for example and without limitation, sonication, crushing, shearing, oxidation, exposure to photonic radiation or chemical (for example, not limited to, enzymic) cleavage of the microorganisms.

In accordance with one or more further embodiments, a medicament comprised of an effective dose of subtilisin is administered to a patient to prevent/treat/cure neurological conditions and diseases. In accordance with one or more embodiments, an effective amount of subtilisin administered will depend upon the severity of the disease process (the subtilisin may be administered in one or more, preferably three, doses daily). However, an effective amount is in a range from about 2,000 fibrinolytic units/day to about 10,000 fibrinolytic units/day. In accordance with one or more further embodiments, a medicament comprised of an effective amount of a non-pathogenic microorganism and/or its spore that are capable of providing subtilisin is administered to a patient to prevent/treat/cure neurological conditions and diseases.

In accordance with one or more embodiments, an effective amount of subtilisin in combination with the *L. bulgaricus* B-30892 strain and/or a supernatant of the *L. bulgaricus* B-30892strain will be administered, and the amount will depend upon the severity of the disease process (the subtilisin and *L. bulgaricus* B-30892 and/or the supernatant may be administered one or more, preferably three, doses daily). An effective amount of *L. bulgaricus* B-30892 contained in the medicament is in a range from about $1 \times 10^5$ to about $1 \times 10^{12}$ colony forming units (CFU) of *L. bulgaricus* B-30892 per day and/or supernatant resulting from culturing about $1 \times 10^5$ to about $1 \times 10^{12}$ colony forming units (CFU) of *L. bulgaricus* B-30892 per day in a cultured liquid and is in a range from about $1 \times 10^5$ to about $1 \times 10^{14}$ colony forming units (CFU) of *L. bulgaricus* B-30892 per day in a powdered form.

In accordance with one or more such embodiments, suitable microorganisms and spores include, for example, but not limited to, *Bacillus subtilis, Bacillus licheniformis*, and *Bacillus lentus* and their various strains. An effective amount of the microorganism and/or its spores is an amount that is effective to cause destruction or deactivation of mimics, immunogens and/or antigens that cause or exacerbate neurological conditions and diseases. In accordance with one or more such embodiments, an effective amount is from about 100 thousand CFU to about 600 billion CFU per dose (CFU designates colony forming units), where the dose is administered about one or more times per week, or as often as about one to about three times daily. In accordance with one or more still further embodiments, a medicament comprised of an effective amount of parts of, or entirely broken up, microorganisms and/or their spores capable of providing subtilisin, is administered to a patient to prevent/treat/cure neurological conditions and diseases. Parts of the microorganisms and/or spores can be separated and selected, using any one of a number of methods that are well known to those of ordinary skill in the art, for their bioactive properties to help ensure and improve the rate of the destruction or deactivation of mimics, immunogens or immunogens that cause or exacerbate neurological conditions and diseases and/or to improve the effectiveness of enzymes in the gastrointestinal or respiratory tract in destroying or deactivating such mimics, immunogens and/or antigens.

In accordance with one or more embodiments, the above-described medicaments can be administered or delivered orally or via the nose or by suppository or by injection into a patient's gut (for example, and without limitation, by enema, endoscope, colonoscope, robotically actuated capsule, and so forth), to act as a prophylactic in the upper respiratory and/or gastrointestinal tract to prevent/treat/cure neurological conditions. As used herein, oral delivery includes, for example and without limitation, a capsule; a tablet; a chewable tablet/capsule; a spray; a gel, a liquid drink, a food, a powder, a gum, a candy, or cream containing the product. The term orally delivery includes sublingually, and on an absorbent substrate or adsorbent substrate. In accordance with one or more embodiments, a medicament can be administered rectally, where a rectal delivery mechanism includes, for example and without limitation, an enema, a fecal transplant, a gel, a cream, an ointment, or a suppository. A fecal transplant includes at least some of the following. First, a donor of feces is screened to look for parasites, pathogenic microorganisms, and to measure the kinds of microbes that are in the donor's feces. The donor's feces are also analyzed for chemicals having, for example, but not limited to, proteolytic activity. Next, the microbial and chemical measurements are compared against a set of requirements for a successful transplant, for example, but not limited to, the presence of bacteria or chemical activity that can destroy mimics, immunogens and/or antigens that cause or exacerbate neurological conditions and diseases. Next, the donor's feces may be corrected for pH level by adding acids, bases, or appropriate buffering agents. Any imbalance of enzymes may be corrected by selecting an appropriate enzyme or pro- or co-enzyme producing microbe. A candidate microbe may be identified in the manner described below. Next, undesirable bacteria can be neutralized or killed. If the donor's feces do not have sufficient ability to destroy mimics, immunogens and/or antigens that cause or exacerbate neurological conditions and diseases, then microorganisms that are capable of destroying mimics, immunogens and/or antigens that cause or exacerbate neurological conditions and diseases, are added, in an effective amount, to the donor's feces prior to a fecal enema or around the time of the fecal enema to populate the sick person's gastrointestinal tract.

In accordance with one or more embodiments, the above-described medicaments can be administered transdermaly, where a transdermal delivery mechanism includes, for example and without limitation, a skin patch, a spray, a gel, a cream, an ointment or a bath. In accordance with one or more embodiments, the above-described medicaments can be administered intravenously, where intravenous delivery includes, for example and without limitation, injection of the medicament mixed into an intravenous solution. In accordance with one or more embodiments, the above-described medicaments can be administered by inhalation, where intravenous delivery includes, for example and without limitation, a nebulized powder inhaled by the nose or mouth.

In accordance with one or more such embodiments, treatment may range from about weekly to about daily, and be ongoing until symptoms of neurological conditions and diseases have disappeared.

The following describes methods for preparing useful microorganisms. Fermentation: As an example, microorganism *Bacillus subtilis* Natto produces the endoprotease subtilisin. Fermentation additives may be added to a culture of the microorganisms to enhance: production of microorganisms, ability of the microorganisms to survive in the gastrointestinal tract, ability of the microorganisms to adhere to the gastrointestinal tract, ability of the microorganisms to secrete desired proteases, ability of the microorganisms to secrete chemicals to enhance survival of proteases, ability of the microorganisms to secrete chemicals to enhance effectiveness of desired proteases, and ability of the microorganisms to secrete chemicals to interfere with undesired chemicals. Also, the amount and kinds of sugars, vitamins, amino acids, proteins and/or fats available to the microorganisms, prior to drying and forming a powder, affect their viability. Examples of useful sugars are, but are not limited to, sucrose, fructose, glucose, lactose, trehalose, raffinose, paliainose, lactulose, lactitol, xylitol, sorbitol, mannitol, malstose, dextrin and maltodextrin. Examples of useful anti-oxidants are, but are not limited to, ascorbic acid, glutathione and alpha-lipoic acid. Examples of useful amino acids or their salts are, but are not limited to, lysine, cysteine, glycine and glutamate. Examples of useful oils are, but are not limited to, butter, palm oil, nut oil, cocoa oil, rapeseed oil and soy bean oil. Examples of useful stabilizing ingredients are, but are not limited to, soybean oligosaccharides, frutooligosaccharides, galactooligosaccharides, galactosyl lactose, milk, milk powders, whey, whey protein concentrates, casein, casein hydrolysates, lactoferrin, lactoperoxidase, lactoglobulins, glymacropeptides, lacto-saccharides, glycomacropeptides, lacto-saccharides and lacto-lipids. Examples of vitamins are, but are not limited to, vitamin D3 and vitamin E.

A chemical that inactivates an enzyme is, for example and without limitation, a serpin. Thus, it is desirable to inhibit serpins that inactivate proteases that destroy mimics, antigens, or immunogens that cause autoimmune disease. Also, protective agents such as, for example and without limitation, cryoprotectants or other chemicals such as gels, starches, polysaccharides, and/or sugars can be added to the culture to protect the microorganisms during the manufacturing processes.

Removing Liquid: When a powdered form of a microorganism is required, the microorganisms need to have liquid removed. One option, known to those of ordinary skill in the art, is to centrifuge the fermentation mixture to reduce the amount of liquid. Other options include, but are not limited to, settling and membrane filtration. This concentrates the microbes by separating them from their supernatant. As such, it allows for more microbes per kilogram of dried product to keep transportation and storage costs down and to deliver more microbes per capsule or pill. It also allows the microbes to be added as a concentrated powder to be mixed into a drink or sprinkled onto food. Centrifuging is beneficial when the supernatant does not contain substantial amounts of bioactive substances that the microbes cannot readily secrete or create in the gastrointestinal tract. However, if the supernatant has the bioactive substances for therapeutic effect, then centrifuging does not need to be performed if the microbes are still desired. In some cases, centrifuging or other separation processes, known to those of ordinary skill in the art, may be desired to obtain the bioactive substances, such as enzymes or bacteriocins, for delivery without the microbe. The following methods may also be used to separate microorganisms from supernatant: sedimentation, ultrafiltration and reverse osmosis.

Drying: This step dries the microorganisms as well as any available supernatant. The microorganisms can be dried with freeze-drying techniques, known to those of ordinary skill in the art, by placing the centrifuged microbes and residual supernatant, which form a slurry, onto trays and freezing them in a vacuum environment. After the slurry dries, it resembles a cake. The dried cake is then crushed, and the crushed powders are sieved to obtain the desired particle size distribution. This process of drying in bulk followed by crushing often kills many bacteria due to the thermal and mechanical stresses applied to the microbes. Another method of making a powder, known by those of ordinary skill in the art, is to spray dry the microorganisms. For this process the slurry is sprayed through a nozzle into a heated air environment. The incoming slurry can be heated or unheated. If the shear forces and temperatures that the microorganisms and/or enzymes experience during the heated spray drying process are too great, microorganisms will die or be damaged enough that the intended therapeutic effectiveness of the microorganism and/or enzyme will be diminished. To improve the yield and prevent damage to surviving microorganisms, an electrospray drying process can be used. Examples of manufacturers who make suitable electrospray drying equipment are Charge Injection Technology and Zoom Essence.

Drying of Supernatant Without Microbes: This step dries the supernatant with the microorganisms removed. The microorganisms can be removed with separation techniques, known to those of ordinary skill in the art, by placing the supernatant, onto trays and freezing them in a vacuum environment. After the supernatant dries, it is then crushed, and the crushed powders are sieved to obtain the desired particle size distribution. Another method of making a powder, known by those of ordinary skill in the art, is to spray dry the supernatant. For this process the supernatant is sprayed through a nozzle into a heated air environment. The incoming supernatant can be heated or unheated. To improve control of the particle size distribution and other properties of the powders, an electrospray drying process can be used. Examples of manufacturers who make suitable electrospray drying equipment are Charge Injection Technology and Zoom Essence.

Blending: Other ingredients, such as but not limited to, dried proteases, microorganisms, protective sugars, polysaccharides, gums, oils, desiccants, anti-oxidants, and bacteriocins, can be added prior to or after the drying process. These ingredients will assist the microbes in surviving during storage as well as in passing to the target areas of the gastrointestinal tract. Also adding other ingredients is needed to reduce the dosage of concentrated microbial powders to the dosages required for delivery to the person.

Delivery: A powder can also be an acceptable delivery system especially when microorganisms do not need to be alive and where either their microbial parts or their secreted bioactive substances are effective against pathogens or for normalizing protease ratios. The powder can be consumed by adding the powder to a food or drink product. The powder containing the microorganisms, and/or supernatant, and/or enzymes can be formulated by those of ordinary skill in the art into a drink that may contain for example, but not limited to, water, sweeteners, flavorings, colorants, anti-oxidants, vitamins, minerals, short-chain fatty acids, stimulants, mood-enhancers, teas, anti-inflammatories, and other bioactive ingredients. The powder can be consumed after sprinkling or pouring it over solid food or mixing into a liquid. The powder can be packaged into bulk containers such as a bag or can or into individual sachets for easy of carrying and single use dosing. To form a tablet, a powder containing the microbes and/or enzyme(s), excipients, and/or other bioactive substances are compressed into a mold in a tableting machine. The tablet can be coated with methods and processes known to those of ordinary skill in the art to prevent the premature dissolution of the product in the stomach to keep the microbes alive for delivery further down the gastrointestinal (GI) tract. Such coatings are designed by those of ordinary skill in the art to dissolve by time in the GI tract or more preferably by pH exposure as the pH along the GI tract is acidic in the stomach and the pH increases by the time the digested contents reach the large intestine. At the large intestine, the pH is approximately 7. Some examples known to those of ordinary skill in the art of a pH triggered coating are, but not limited to, Eudragit and shellac. The tablet can be designed by those of ordinary skill in the art to be consumed orally or inserted into the rectum or vagina as a suppository. To form a capsule, a powder containing the microorganisms, supernatant, enzymes, excipients and/or other bioactive substances are directed into a capsule that can be made of materials known to those of ordinary skill in the art, but are not limited to, hardened gelatin or other polymer. The capsule can be coated by processes known to those of ordinary skill in the art to prevent the premature dissolution of the product in the stomach to keep the microorganisms alive and enzymes effective for delivery further down the GI tract. Such coatings known to those who are of ordinary skill in the art are designed to dissolve by time in the GI tract or more preferably by pH exposure. Some examples known to those of ordinary skill in the art of a pH triggered coating are, but not limited to, Eudragit and shellac. The capsule can be designed by those of ordinary skill in the art to be consumed orally or inserted into the rectum or vagina as a suppository. An alternate form of a capsule to contain the microorganisms, enzymes, excipients, and/or other bioactive substances is a gel capsule that can be made of materials and processes known to those of ordinary skill in the art.

For a liquid delivery system, the microorganisms and/or supernatant and/or enzymes and bioactive substances can be introduced in a fermented liquid. That liquid can be in the form of cultured or non-cultured animal-based and/or plant-based milk such as, but not limited to, cow's, goat's, rice, almond, and/or soy milk. Alternatively, microorganisms and/or enzymes can added to a drink such, as but not limited to, a juice or formulated into a drink that may contain for example but not limited to water, sweeteners, flavorings, colorants, anti-oxidants, vitamins, minerals, short-chain fatty acids, stimulants, mood-enhancers, teas, anti-inflammatories and other bioactive ingredients. For a solid delivery system the microorganisms and/or enzymes and bioactive substances can be added to solid food in accordance with a number of methods that are well known to those of ordinary skill in the art. Examples of such food are, but are not limited to, candy, confectionary, chewing gum, energy bars, fermented/dried vegetables, fermented/dried meat, fermented/dried seafood, fermented/dried fruit, fermented/dried beans and frozen desserts. For a slurry delivery system the microorganisms and/or enzymes and bioactive substances can be added to slurry foods in accordance with a number of methods that are well known to those of ordinary skill in the art. Examples of such food are, but not limited to, yogurt, jams, jellies, gravies, gel shots, puddings, frozen desserts, salad dressings, syrups and spreads.

Since secretions from *L. bulgaricus* B-30892 are known to neutralize toxins and prevent adhesion of bacteria to tissues along the gastrointestinal tract, another embodiment of this invention is to ferment the *L. bulgaricus* B-30892 in a medium and remove the *L. bulgaricus* B-30892 by filtration, centrifugation, or other means known to those of ordinary skill in the art to make a liquid containing the bioactive ingredients from the *L. bulgaricus* B-30892. That liquid can be further concentrated using a filter membrane such as a reverse osmosis or thermal distillation membrane to decrease the fluid volume so that the resulting liquid can be stored in smaller containers. The liquid can also be vacuum-dried, freeze-dried or spray dried to create a powder containing the bioactive ingredients from the B-30892 so that the resulting powder can be made into capsules, tablets, or be used as an ingredient for a nutritional supplement. An effective amount of medicament may result from a volume of liquid, prior to concentrating or drying, that fermented a range from about $1 \times 10^5$ to about $1 \times 10^{14}$ colony forming units (CFU) of *L. bulgaricus* B-30892 per day.

A case report is for an 18 year old male with autistic spectrum disorder and anxiety for more than 10 years. Prior to consuming *L. bulgaricus* B-30892 he suffered from lack of social behavior and anxiety. Within 5 days of consuming 1 cup a day of yogurt containing *L. bulgaricus* B-30892, his mother reported a dramatic reduction in anxiety and his mother observed that he had a substantial improvement in social interactions.

Embodiments of the present invention described above are exemplary, and many changes and modifications may be made to the description set forth above by those of ordinary skill in the art while remaining within the scope of the invention. As such, the scope of the invention should be determined with reference to the appended claims along with their full scope of equivalents.

What is claimed is:

1. A method of mitigating or treating autism spectrum disorder comprises:
 administering an effective amount of a medicament comprised of *Lactobacillus bulgaricus* B-30892 to a human to mitigate or treat autism spectrum disorder.

2. The method of claim 1 wherein the medicament further comprises oligopeptidase F (PepF).

3. The method of claim 1 wherein the medicament further comprises endopeptidase O (PepO).

4. The method of claim 1 wherein the medicament further comprises endopeptidase O2 (PepO2).

5. The method of claim 1 wherein the medicament further comprises subtilisin.

\* \* \* \* \*